(12) United States Patent
Nowel

(10) Patent No.: US 12,012,303 B2
(45) Date of Patent: Jun. 18, 2024

(54) ELEVATOR TRIP PLANNING BASED ON DESTINATIONS AND ACTIVITY PARAMETERS

(71) Applicant: Inventio AG, Hergiswil (CH)

(72) Inventor: Edward Nowel, Columbia, NJ (US)

(73) Assignee: INVENTIO AG, Hergiswil (CH)

( * ) Notice: Subject to any disclaimer, the term of this patent is extended or adjusted under 35 U.S.C. 154(b) by 1244 days.

(21) Appl. No.: 16/079,582

(22) PCT Filed: Feb. 20, 2017

(86) PCT No.: PCT/EP2017/053725
§ 371 (c)(1),
(2) Date: Aug. 24, 2018

(87) PCT Pub. No.: WO2017/144384
PCT Pub. Date: Aug. 31, 2017

(65) Prior Publication Data
US 2021/0179386 A1    Jun. 17, 2021

(30) Foreign Application Priority Data
Feb. 24, 2016 (EP) ................................ 16157061

(51) Int. Cl.
*B66B 1/46* (2006.01)
*A63B 24/00* (2006.01)
(Continued)

(52) U.S. Cl.
CPC .......... *B66B 1/468* (2013.01); *A63B 24/0075* (2013.01); *B66B 1/2408* (2013.01);
(Continued)

(58) Field of Classification Search
CPC . B66B 3/00–006; B66B 1/3492; B66B 1/468; B66B 2201/103; B66B 2201/104
See application file for complete search history.

(56) References Cited

U.S. PATENT DOCUMENTS

| | | | |
|---|---|---|---|
| 5,511,634 A * | 4/1996 | Bahjat | B66B 1/2458 187/385 |
| 8,836,580 B2 | 9/2014 | Mendelson | |

(Continued)

FOREIGN PATENT DOCUMENTS

JP    2009222658 A  * 10/2009

*Primary Examiner* — Christopher Uhlir
(74) *Attorney, Agent, or Firm* — William J. Clemens; Shumaker, Loop & Kendrick, LLP

(57) ABSTRACT

An elevator trip based on destinations and activity parameters of a user is planned by a system having an elevator controller of an elevator installation, a storage device storing building plan data and a route planning computer. The user's trip inquiry, including a desired destination and a desired activity parameter, is received by the planning computer. Building plan data is read from the storage device by the planning computer. The current location of the user is determined by the planning computer, which calculates at least one route proposal based on the user's location, the destination and the activity parameter. The route proposal is communicated to the user. Upon receipt of a confirmation that the user selected the route proposal, a control signal identifying a boarding floor and a destination floor is transmitted by the planning computer to the elevator controller. The elevator installation is controlled according to the control signal.

16 Claims, 5 Drawing Sheets

(51) Int. Cl.
  *B66B 1/24* (2006.01)
  *B66B 1/28* (2006.01)
  *B66B 1/34* (2006.01)
  *B66B 3/00* (2006.01)
  *G01C 21/20* (2006.01)
  *H04W 4/024* (2018.01)
  *H04W 4/029* (2018.01)

(52) U.S. Cl.
  CPC .............. *B66B 1/28* (2013.01); *B66B 1/3461* (2013.01); *B66B 3/006* (2013.01); *G01C 21/206* (2013.01); *H04W 4/024* (2018.02); *H04W 4/029* (2018.02); *B66B 2201/103* (2013.01); *B66B 2201/40* (2013.01); *B66B 2201/4615* (2013.01); *B66B 2201/4638* (2013.01); *B66B 2201/4653* (2013.01)

(56) References Cited

U.S. PATENT DOCUMENTS

| | | | |
|---|---|---|---|
| 8,915,334 B2* | 12/2014 | Finschi | B66B 1/34 |
| | | | 187/901 |
| 9,873,590 B2* | 1/2018 | Salmikuukka | B66B 1/46 |
| 10,571,276 B2* | 2/2020 | Khan | G06F 3/04815 |
| 10,597,255 B2* | 3/2020 | Chapman | B66B 1/3461 |
| 10,889,463 B2* | 1/2021 | Chapman | B66B 3/006 |
| 2014/0278229 A1 | 9/2014 | Hong et al. | |
| 2015/0048953 A1* | 2/2015 | Murphy, Jr. | G01C 21/206 |
| | | | 340/691.6 |
| 2015/0377635 A1* | 12/2015 | Beaurepaire | G05D 1/021 |
| | | | 701/408 |

\* cited by examiner

ELEVATOR TRIP PLANNING BASED ON DESTINATIONS AND ACTIVITY PARAMETERS

FIELD

The present disclosure of various embodiments generally relates to assisting a person to navigate through a building having at least one elevator installation. More particularly, the various embodiments described herein relate to a system that plans a person's route including an elevator trip and a method of operating such a system.

BACKGROUND

Multi-story buildings are usually equipped with at least one elevator installation that provides for vertical transportation. In a generally known elevator installation, a suspension medium—such as a rope or flat belt-type rope—interconnects a counterweight and a car, and an electrical drive motor causes the suspension medium to move in order to thereby move the counterweight and the car up and down along a shaft or hoistway. An elevator controller of the elevator installation controls and monitors the operation of the elevator installation, e.g., by processing elevator calls and allocating elevator cars to these calls.

Multi-story buildings not only extend in vertical direction, but may have a substantial horizontal extension as well. In combination, the vertical and horizontal extensions may make orientation difficult, in particular for visitors that are not familiar with the building and its layout. To facilitate orientation within buildings, U.S. Pat. No. 8,836,580 discloses radiofrequency proximity tags that provide for indoor and outdoor navigation in combination with mobile phones that execute an indoor navigation application. Location information received from these tags is displayed on the mobile phone's display as an overlay over an area map. As suitable indoor navigation technologies, U.S. Pat. No. 8,836,580 discloses WLAN (IEEE 802.11b) and Bluetooth (IEEE 802.15).

Even though U.S. Pat. No. 8,836,580 provides navigation information conveniently on a user's mobile phone, the technology is limited to guiding the person from a starting point to a destination location. Certain users may, however, require additional assistance or information. There is, therefore, a need for an improved technology that provides additional assistance and information to a user and, yet, reliably guides the user to the desired destination.

SUMMARY

Accordingly, one aspect of such an improved technology involves a method of controlling a system having an elevator controller of an elevator installation in a building, a storage device storing building plan data and a route planning computer. A trip inquiry from a user at a current location within the building is received by the route planning computer, wherein the trip inquiry includes a desired destination and a desired activity parameter. Building plan data is read from the storage device by the route planning computer, wherein the building plan data concern at least one of locations of building access doors, hallways, stairs, designated areas, and elevator landings. The current location of the user within the building is determined by the route planning computer, which calculates at least one route proposal based on the current location of the user, the desired destination and the desired activity parameter. The at least one route proposal is communicated by the route planning computer to the user. Upon receipt of a confirmation indicative of the user selecting the at least one route proposal, a control signal identifying a boarding floor and a destination floor is transmitted by the route planning computer to the elevator controller. The elevator installation is controlled by the elevator controller according to the control signal.

Another aspect of the alternative technology involves a system having an elevator controller, a storage device and a route planning computer. The elevator controller controls an elevator car to transport a user from one floor to another floor of the building, wherein the user carries a mobile electronic device allowing setting up a user-specific inquiry concerning a desired user activity and a desired destination within the building. The storage device stores building plan data concerning at least one of locations of building access doors, hallways, stairs, designated areas, and elevator landings. The route planning computer is coupled to the elevator controller and the storage device. Upon receipt of a user-specific inquiry concerning a desired user activity, and a desired destination, the route planning computer determines at least one route proposal based on the building plan data, the desired user activity, and the desired destination. The route planning computer communicates the at least one route proposal to the user for the user to confirm selection of the at least one route proposal. Upon receipt of a confirmation indicative of the user selecting the at least one route proposal, the route planning computer transmits a control signal identifying a boarding floor and a destination floor to the elevator controller. The elevator controller controls the elevator installation according to the control signal.

The technology described herein processes health/fitness-based goals of a user, and information available within a building to control the elevator installation. The user wears or carries a fitness tracker which tracks the user's activity, and allows the user to set individual health/fitness goals. The fitness tracker may be a dedicated device for that purpose, or another mobile electronic device such as smart phone, or smart watch provided with a dedicated software application and coupled to a sensor worn by the user. The user's goal can be expressed as an activity parameter, which is in one embodiment a desired number of steps. For an average user, the number of steps is a reliable indicator of the user's activity during a certain period of time, e.g., a day. Depending on the user's fitness goals, the technology presents the user with route options that require the user to walk more or less steps. Accordingly, elevator trips that are part of the route options bridge more or less floors of the building.

In one embodiment, the at least one route proposal is conveyed to the user using a user interface. The user interface may be comprised in a user input device, such as a floor terminal or a mobile electronic device. The user interface can display the at least one route proposal as text and/or at least one symbol, or announce the at least one route proposal as an audio message. The user interface, therefore, provides flexibility with respect to the user's preferences or requirements, for example, the visually impaired user may prefer or require an audio message.

Flexibility also exists with respect to determining the current location of the user. In one embodiment, the current location is determined using an indoor positioning system. Various techniques are known to determine the position of the user within the building, such as Wi-Fi access point, or Bluetooth technology. The current location of the user may also be determined by identifying a location of the user input device (e.g. a floor terminal) involved in communicating the trip inquiry to the route planning computer. Since the location of the user input device (floor terminal) is documented in the building plan data, the location of the user is assumed to be at that user input device (floor terminal).

An additional aspect of flexibility relates to the time the technology is available to the user. For example, at times of high traffic within the building, handling the building traffic efficiently takes priority over individual fitness goals. Accordingly, in one embodiment, the route planning computer, or its function, can be disabled. This includes, for example, disabling entry of trip inquiries at floor terminals, or announcing the unavailability of the fitness mode, e.g., by means of displays at the floor terminals or other locations within the building.

Times of high traffic may exist, e.g., during lunch time. This is a popular time for office workers to leave the building and, for the more health conscious one, to combine this with some exercise. To avoid disabling the fitness mode, the route planning computer takes into account the elevator installation's traffic situation and generates at least one route proposal that serves both the user's trip inquiry and the current high-traffic situation. In view of the trip inquiry, the route planning computer checks if an already planned elevator trip can be used to transport the user. In these examples, the fitness mode is maintained, but the trip-inquiry triggered individual scheduling of elevator trips is restricted during times of high traffic.

Once the user receives and confirms the at least one route proposal, additional information may be provided to the user to facilitate the user's orientation within the building along the selected route proposal. For that purpose audio and/or visual indicators may be provided that serve to guide the user along the selected route proposal.

DESCRIPTION OF THE DRAWINGS

The novel features and method steps characteristic of the technology are set out below. The various embodiments of the technology, however, as well as other features and advantages thereof, are best understood by reference to the detailed description, which follows, when read in conjunction with the accompanying drawings, wherein.

DETAILED DESCRIPTION

Figure 1:
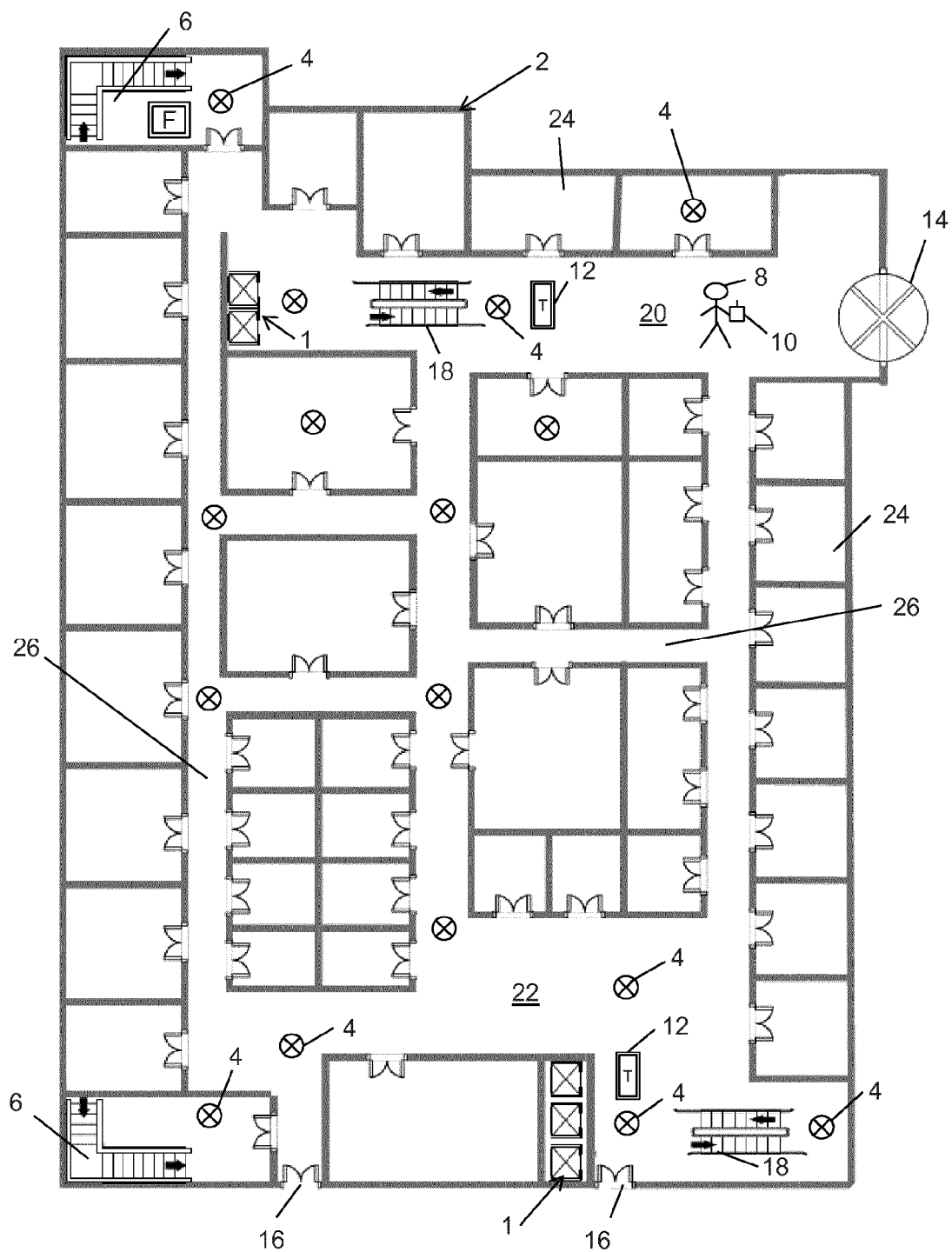
FIG. 1 shows a schematic illustration of an exemplary situation on a building floor served by elevator installations.
Figure 2:
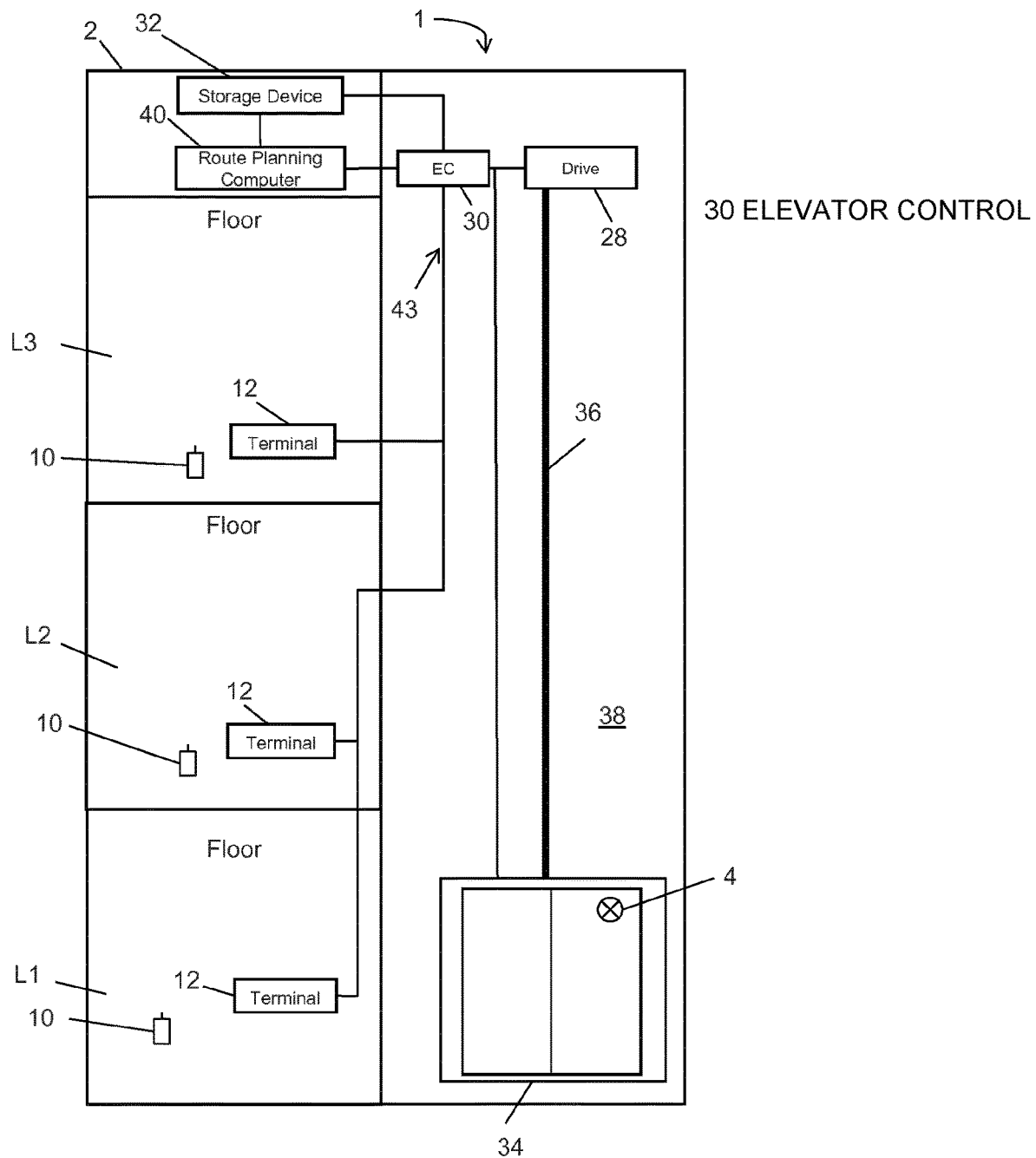
FIG. 2 shows a schematic illustration of a side view of a part of the building together with details of an exemplary elevator installation.
Figure 3:
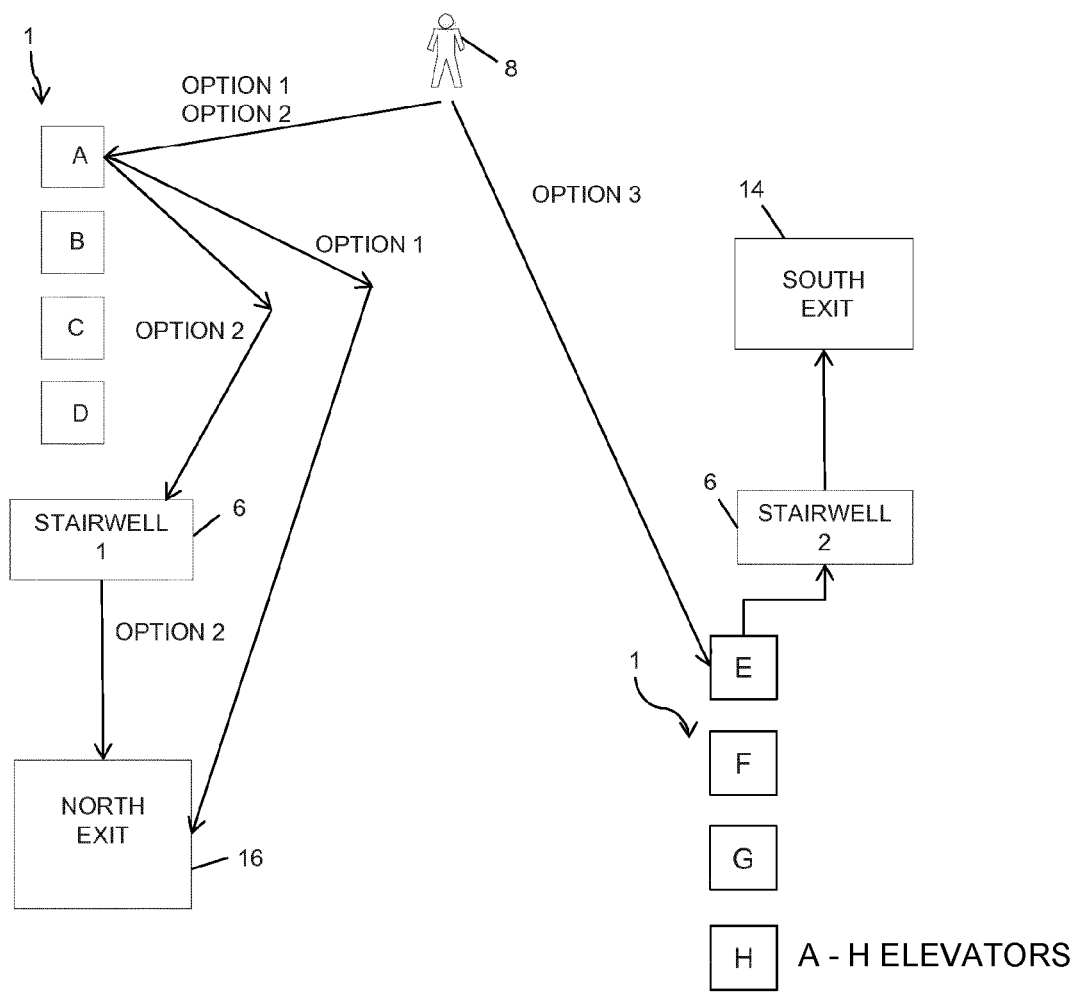
FIG. 3 is a schematic illustration of various route options within the building.

FIG. 1 is a schematic illustration of an exemplary situation on a floor of a building 2, in particular a multi-story building, and FIG. 2 illustrates one embodiment of a part of the building 2 in vertical direction. The horizontal and vertical building situations shown in FIG. 1 and FIG. 2 may be documented in the building's documentation, which may include a building plan, one or more floor plans, and/or a building model. The building 2 may be an apartment building, an office building, a commercial/shopping center, a hotel, a sports arena, an airport terminal, a ship, or any other structure suitable for a person to reside or stay for a longer period of time. The exemplary building 2 shown in FIG. 1 and FIG. 2 is used herein to describe various embodiments of the technology; it has a main entrance 14 and two side entrances 16 through which persons can enter and leave the building 2. Depending on a particular embodiment, the building 2 may have more than one main entrance 14. To assist orientation, names or labels may be assigned to the entrances 14, 16, such as south entrance, or north entrance, as indicated in FIG. 3.

The main entrance 14 leads to a lobby 20, and the side entrances 16 lead to a lobby 22. Each lobby 20, 22 allows a user or person 8 to access an elevator installation 1, an escalator installation 18, and a stairwell 6 to reach another floor of the building 2. Further, each lobby 20, 22 allows the person 8 to walk into corridors and hallways 26 and individual rooms 24. User input devices, hereinafter also referred to as floor terminals 12, are located in the lobbies 20, 22, e.g., in proximity of the elevator installations 1, and allow a person 8 to call an elevator. Similar situations may exist on other floors as well. In the illustrated embodiment, the person 8 is currently located in the lobby 20, and wears or carries a mobile electronic device 10. The terms "user" and "person" are used herein interchangeably.

In one embodiment, the mobile electronic device 10 may be an activity/fitness tracking device (hereinafter referred to as fitness tracker) that tracks and records a user's activity, such as the number of steps the user takes during a certain period of time. Such a fitness tracker is available, e.g., from Fitbit, Inc., or Jawbone. One example of a fitness tracker is described in publication number US 2014/0278229 A1. A user typically wears such a fitness tracker around the wrist of an arm, which allows the user to look at and to manipulate a user interface of the fitness tracker. For charging and/or set up, such a fitness tracker can be coupled to a computer that provides a more convenient user interface. In another embodiment, the mobile electronic device 10 may be a mobile phone, smart phone, or tablet PC that run certain user-selected and/or user-activated software applications, also referred to as apps. A smart phone, for example, may include a sensor, or be coupled to a sensor worn by the user, that senses a characteristic (e.g., acceleration of the sensor, or the user's heartbeat) associated with the user's activity, whereas the software application processes the acquired sensor data. Such a combination of a smart phone and a sensor functions as a fitness tracker, wherein the smart phone's user interface serves—supported by the fitness tracker software application—as the user interface of the fitness tracker.

Focusing initially on the general operation and certain features of the technology, and describing its structural details thereafter, the technology allows the user 8, who is equipped with such a fitness tracker, not only to be guided to a desired destination within the building 2, but also allows the user 8 to achieve a personal activity goal or target while on the way to a desired destination. Briefly, to achieve that objective, the technology combines the health/fitness-based goals of using a fitness tracker with information available within the building 2, such as passenger location, building layout, available transportation means, and distances within the building 2. In some embodiments, the technology may determine various options (e.g., routes) for achieving the desired activity goal, and communicate these options to the user 8.

FIG. 3 illustrates on a high level various route options within the building 2, as determined by the technology as a function of the user's current location, desired destination, and activity goal. The route options are labeled as "Option 1", "Option 2", and "Option 3" and indicated through arrows. FIG. 3 shows further individual elevators A
  H of the elevator installation 1, stairwells 6 (labeled as "Stairwell 1" and "Stairwell 2"), the main entrance 14 (labeled as "South Exit"), and a side entrance 16 (labeled as "North Exit").

In one exemplary situation, the user 8 wishes to leave an office on an upper floor and go out to lunch, e.g., at a restaurant. Before leaving, the user 8 asks (using the mobile electronic device 10) for options how to best exit the building 2 having in mind a certain activity goal. In view of the user's intent, the technology uses the building documentation to determine route options. The technology communicates these route options to the user 8 using a user input device, e.g., one of the floor terminals 12 or the mobile device 10. In option 1, the user 8 may receive an indication such as: "800 steps if you take elevator A to the lobby, and then go out the north exit". In option 2, the user 8 may receive an indication such as "1,200 steps if you take elevator A to the 3rd floor, take stairwell 1 down to the lobby, and then go out the north exit". In option 3, the user 8 may receive an indication such as "1,600 steps if you take elevator E to the 2nd floor, walk around to the rear of the building, take stairwell 2 down to the lobby, and then go out the South exit". In one embodiment, the technology presents these options to the user 8, and the user 8 can select one of these options.

In one embodiment, the technology allows the user 8 to request a certain number of steps to a specific destination. For example, the user 8 may request at least 1,200 steps within the building 2 on the way to the restaurant. In view of the user's 8 intent and activity goal, the technology determines one or more options that closely approximate the user's step request. In the embodiment shown in FIG. 3, the technology communicates at least option 2 to the user 8 because this option comes closest to the user's request of 1,200 steps. It is contemplated that option 3 can be communicated to the user 8 as well because it also meets the user's request of at least 1,200 steps.

Figure 4:
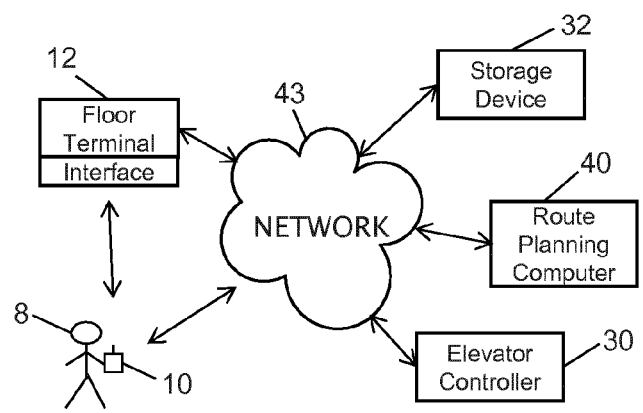
FIG. 4 is a schematic illustration of interactions between a user and components of a system having an elevator controller of the elevator installation in a building, a storage device storing building plan data, and a route planning computer building by means of a network.

The technology described herein is implemented in a system having a route planning computer 40, an elevator controller 30, and a storage device 32. The system is in the illustrated embodiment of FIG. 2 located within the building 2. It is contemplated, however, that in certain embodiments at least the route planning computer 40 or the storage device 32 may be located remote from the building 2. In the illustration of FIG. 2, the elevator controller 30 is further coupled to a drive 28, which moves the elevator car 34 by means of suspension member 36 up and down a shaft 38. Independent of the specific locations of the route planning computer 40, the elevator controller 30, and the storage device 32, these system components are communicatively coupled to each other by means of a network 43, as shown in FIG. 4. The floor terminals 12 and the mobile electronic device 10 are in one embodiment also coupled to the network 43, whereas the mobile electronic device 10 may communicate with the floor terminals 12, as indicated in FIG. 4. In FIG. 4, the floor terminal 12 is shown as having a user interface. The network 43 may be any known wired and/or wireless communications network that allows communications between the components of the system. The network 43 may include a LAN, a WAN, the internet, which may include wired or wireless networks, and/or a cellular communications network for mobile communications, such as for UMTS or 4G. Within the building 2, the network 43 may operate according to a LON or the BACnet protocol.

Referring again to FIG. 2, FIG. 2 illustrates a lateral view of a part of the building 2 together with one embodiment of the elevator installation 1. FIG. 2 does not show the escalator installations 18 shown in FIG. 1, however, it is contemplated that an escalator installation 18 also provides for vertical transportation of persons. The illustrated part of the building 2 has several floors L1, L2, L3, each one providing access to an elevator car 34. That is, the person 8 can board the elevator car 34 on one of these floors L1, L2, L3 (hereinafter referred to as boarding floor), and, after having been transported to another one of these floors L1, L2, L3 (hereinafter referred to as destination floor), exit the elevator car 34 at the destination floor.

The elevator installation 1 shown in FIG. 2 is in one embodiment equipped with a destination call control system, whereby the user 8 enters the desired destination floor at a floor terminal 12 provided on each floor L1, L2, L3. As is known in the elevator field, such a destination call identifies the boarding floor and the destination floor. In another embodiment, the elevator installation 1 is equipped with a conventional control system, where a floor terminal with up/down buttons is installed on each floor L1, L2, L3, and a car terminal is installed inside each elevator car 34. In such a system, the user 8 initially presses an up or down button on a floor terminal 12 to call the elevator car 34 to the boarding floor, boards the elevator car 34 assigned to serve that call, and then presses a button on a car terminal after boarding the elevator car 34. The technology is herein described with reference to a destination control system implemented, e.g., in the elevator controller 30.

In one embodiment, the user 8 can enter a destination call by pressing a button of a user interface of the floor terminal 12. In another embodiment, a destination call can be entered by means of an information carrier, for example, shaped as a credit card or an employee badge, placed at or in proximity of a floor terminal 12, or inserted into a floor terminal 12. Depending on a particular technology, the information carrier may contain a memory chip with contact pads visible on an exterior surface of the information carrier, an RFID transponder coupled to a memory chip embedded in the information carrier, a magnetic strip, or an optical code applied to an exterior surface of the information carrier, such as a QR code, a barcode, or other machine-readable code. The function of such an information carrier may also be implemented on the mobile electronic device 10. In some embodiments, the mobile electronic device 10 may display a QR code, a barcode, or a color pattern code (e.g., WO2015049186A1). The mobile electronic device 10 may further be equipped with RFID, NFC (near field communication), or Bluetooth technology to communicate with a floor terminal 12.

The floor terminal 12 includes in one embodiment a reader (e.g., as part of the terminal's user interface) that is compatible with the technology used by the information carrier (e.g., a camera or scanner to read an optical code, or an RFID reader to communicate with an RFID transponder). If the user 8 places, for example, the information carrier against the reader of the floor terminal 12, the reader reads in one embodiment an identification code stored on the information carrier. The identification code may be linked to a specific user 8 in a user profile. The user profile may be stored in the storage device 32, and may contain certain user preferences, such as default destination floor, VIP status, or access rights.

As the locations of the floor terminals 12 are fixed and documented in the building's documentation, the elevator controller 30 "knows" which one of the floor terminals 12 the user 8 used to enter the destination call, and, hence, knows the location of the user 8. The elevator controller 30 communicates that location information to the route planning computer 40. Alternatively, the location information may be stored in the storage device 32, and then be read by the route planning computer 40. In certain embodiments, the location of the user 8 can be determined by means of a positioning system, for example, an indoor positioning system. An indoor positioning system can be based on Bluetooth beacons, RFID tags, or Wi-Fi access points.

One example of an indoor positioning system is based on Bluetooth beacons that interact with a Bluetooth enabled mobile electronic device 10. FIG. 1 shows a number of beacons 4 mounted at different locations within the building 2. The beacons 4 are mounted, for example, in areas where the person 8 may be located; this includes the rooms 24, the corridors and hallways 26, the stairwells 6, and the lobbies 20, 22. For ease of illustration, FIG. 1 shows only a few of these beacons 4, and only some of them are identified by reference numerals. The locations of these beacons 4 may also be documented in the building's documentation, wherein each beacon 4 is identified by a unique identification code (e.g., "ID=5"). For example, the beacon 4 may transmit at regular time intervals its identification code. If the mobile electronic device 10 is in proximity of such a beacon 4, the mobile electronic device 10 receives the beacon's identification code. The software application running on the mobile electronic device 10 is in one embodiment configured to communicate the received identification code to the route planning computer 40. The route planning computer 40 then uses the received identification code to determine the location of the beacon 4, as documented in the building's documentation (e.g., "ID=5" located in lobby 20), and to map the beacon's location to the user's location.

Figure 5:
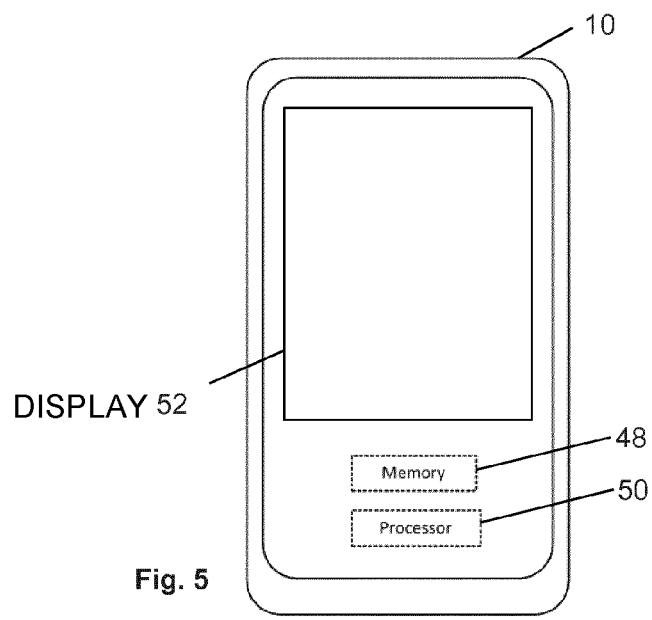
FIG. 5 is a schematic illustration of a mobile electronic device.

FIG. 5 illustrates a smart phone as one example of a mobile electronic device 10. It includes a memory 48 and a processor 50 arranged underneath a display 52, which may be a touch screen. As the memory 48 and the processor 50 are not visible, these components are shown in dashed lines. By means of a user interface the user 8 can select settings and functions directly at the mobile electronic device 10, and thereby adjust the smart phone to personal preferences. For example, the user 8 can activate and deactivate the Bluetooth function, the latter for privacy reasons because without the Bluetooth function being enabled, movements and locations of the person 8 within the building 2 may not be tracked. In addition, the user 8 can activate or deactivate the software application that provides for the fitness tracker function.

With the software application providing for fitness tracker function being enabled, the smart phone as the exemplary mobile electronic device 10 conveys in response to the person's trip inquiry trip information determined by the route planning computer 40, including route proposals or options, to the person 8. The trip information may be announced through a speaker or displayed on the display 52, e.g., as text, graphical symbols (e.g., arrows), maps, and/or pictures of selected locations. The trip information informs/instructs the person 8 where to go next and/or how far it is to the destination. As the route inside the multistory building 2 likely requires the use of the elevator installation 1, the trip information may identify which elevator the person 8 should use, when the elevator arrives at the person's boarding floor and/or how long the waiting time is until the elevator arrives at the boarding floor.

The route planning computer 40 is communicatively coupled to the elevator control 30 and the storage device 32, and includes one or more processors coupled to an internal memory. The internal memory includes one or more computer-readable storage media storing software instructions. The computer-readable storage media can comprise, for example, one or more of optical disks, volatile memory components (such as DRAM or SRAM), or nonvolatile memory components (such as hard drives, Flash RAM or ROM). When executed by the processor, the software instructions cause the processor to perform one or more of the method acts disclosed herein. In particular embodiments, the route planning computer 40 may work with one or more other computers, which are located locally, remotely, or both. One or more of the disclosed methods can thus be performed using a distributed computing system. The software instructions code an algorithm for planning routes within a building. One example of a route planning algorithm is disclosed in: Pu, S. and Zlatanova, S., "Evacuation Route Calculation of Inner Buildings", "Geo-Information For Disaster Management", First International Symposium on Disaster Management, pages 1143-1161, Springer, 2005.

Figure 6:
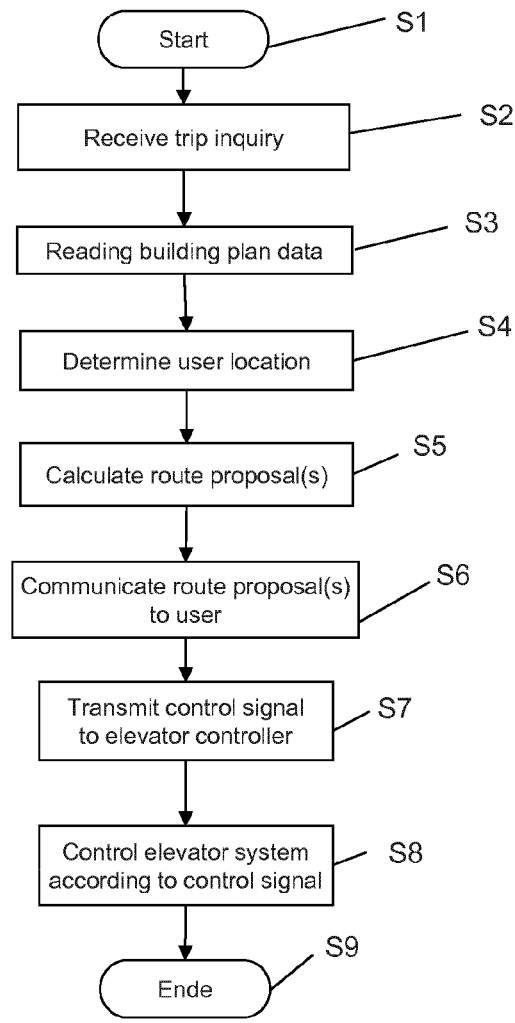
FIG. 6 is a flow diagram of one embodiment of a method of operating the system of FIG. 4.

With the understanding of the general structure of the system and certain features of its components described with reference to FIG. 1-FIG. 5, a description of how one embodiment of the system operates follows with reference to FIG. 6. FIG. 6 shows a flow diagram of one embodiment of a method of operating the system including the elevator controller 30, the storage device 32, and the route planning computer 40. It is assumed that the user 8 is inside the building 2, and carries or wears a mobile electronic device 10, e.g., a fitness tracker, or a smart phone with a fitness tracker function being enabled. It is contemplated that in another illustration of the flow diagram some of the shown steps may be merged into a single step, or split into several separate steps. The flow diagram starts at a step S1 and ends at a step S9.

In a step S2, the route planning computer 40 receives a trip inquiry from the user 8 located at a current location within the building 2. The trip inquiry, as defined by the user 8 using the mobile electronic device 10, includes a desired destination and a desired activity parameter. The desired destination may be a location within the building 2, for example, one of the entrances 14, 16, or a specific room 24. The desired activity parameter may indicate steps, either expressed as the desired number of steps on the way to the desired destination, or a request for route options with particular identification of the number of steps for each option. As described above with reference to FIG. 3, the user 8 may ask for options how to best exit the building 2 having in mind a certain activity goal, i.e., a certain number of steps. For example, the user 8 may have a personal goal of taking at least 10,000 steps a day. If the user's fitness tracker indicates around lunchtime that several thousand steps are still missing, the user 8 may want the route options to include the number of steps. The user 8 can then select the route option with the number of steps that suits the user's current situation best (e.g., the user 8 may have more or less time available). It is contemplated that in another embodiment the activity parameter may be time, e.g., expressed as the (minimum, maximum, or desired) walking time.

Proceeding to a step S3, the route planning computer 40 reads building plan data from the storage device 32. Since the storage device 32 stores the building documentation including the building plan, i.e., digital data representing the building plan, the building plan data concern locations of building access doors or entrances (the main entrance 14, and the side entrances 16), corridors and hallways 26, stairwells 6, designated areas, and elevator landings. It is contemplated that in another embodiment the building plan data may be stored in an internal memory of the route planning computer 40. In that case, the route planning computer 40 (i.e., its processor executing the route planning function) reads the building plan data from the internal memory, or accesses the internal memory to extract selected building plan data.

Proceeding to a step S4, the route planning computer 40 determines the current location of the user 8 within the building 2. The current location of the user 8 may be determined in various ways. If the user 8 uses one of the floor terminals 12 for entering the trip inquiry, or the user's mobile electronic device 10 interacts (e.g., via Bluetooth or NFC communications) with one of the floor terminals 12, the elevator controller 30 knows which floor terminal 12 is involved, and, therefore, knows the location of the user 8. If an indoor positioning system, such as one based on Bluetooth beacons 4, is used, the mobile electronic device 10 transmits in one embodiment the received identification code of a Bluetooth beacon 4 to the route planning computer 40. The route planning computer 40 then queries the building plan data to determine the location of the beacon 4 with that identification code.

Proceeding to a step S5, the route planning computer 40 calculates at least one route proposal based on the current location of the user 8, the desired destination and the desired activity parameter. For that purpose, the route planning computer 40 executes an algorithm for planning routes within a building, as described above. If the trip inquiry includes a request for route options with particular identification of the number of steps for each option, the route planning computer 40 provides in one embodiment several route proposals, such as the three options described above with reference to FIG. 3. Although it may not always be the case, the route proposals shown in FIG. 3 involve use of an elevator. For each route proposal, the route planning computer 40 determines the boarding floor and the destination floor.

Proceeding to a step S6, the route planning computer 40 communicates the at least one route proposal to the user 8. If a floor terminal 12 is involved in entering the trip inquiry, the route planning computer 40 communicates with that floor terminal 12 (e.g., the route planning computer 40 may address a data package to the floor terminal 12), and causes the floor terminal 12 to convey the at least one route proposal to the user 8. The floor terminal 12 may display the at least one route proposal on the display of the floor terminal 12, or announce it via a speaker of the floor terminal 12. If the user 8 used the mobile electronic device 10 to enter the trip inquiry, the route planning computer 40 may transmit the at least one route proposal to the mobile electronic device 10 using a wireless communications technology. In one embodiment, the user 8 confirms the at least one route proposal, either on the floor terminal 12 or on the mobile electronic device 10. If there are more than one route proposal, the user 8 selects one of the route proposals, and, thereby, confirms the selected route proposal. Either way, the confirmation is transmitted to the route planning computer 40.

Proceeding to a step S7, upon receipt of the confirmation indicative of the user 8 selecting the route proposal, the route planning computer 40 transmits a control signal to the elevator controller 30. The control signal identifies the boarding floor and the destination floor which are associated with the route proposal. In one embodiment, the control signal may indicate the time when the elevator car 34 should be at the boarding floor. The time may indicate an immediate need for an elevator car 34 because the user 8 is already waiting at the elevator landing, or that an elevator car 34 is needed at a certain time in the future (e.g. expressed in seconds or minutes) because the user 8 is still a determined distance away from the elevator landing, and not yet ready to board the elevator car 34. Based on the determined distance, the walking time to the elevator landing can be estimated.

Proceeding to a step S8, the elevator controller 30 controls the elevator installation 1 in accordance with the control signal. The control signal may be considered as a destination call that specifies the boarding floor and the destination floor. In response, the elevator controller 30 allocates an elevator car 34 to service that call. Algorithms to allocate elevator cars or elevators are known in the field of elevator technology. For example, if the user 8 selects option 3 shown in FIG. 3, the elevator controller 30 allocates elevator E.

It is contemplated that the method described with reference to FIG. 6 may be adapted to various situations within the building 2 and preferences of the user 8. For example, the building 2 may experience times of high traffic generally or only in certain areas of the building 2. During such high-traffic times, operating the elevator installation 1 and handling the traffic as efficiently as possible has priority over individual personal fitness goals. For that reason, the operational (fitness) mode described with reference to FIG. 6 may not be available during high-traffic times. This may be achieved by, e.g., disabling the route planning computer 40. The time periods during which the fitness mode is not available may be programmed in the system. If the user 8 enters, or attempts to enter a trip inquiry, the system may communicate a message to the user 8 that the fitness mode is currently not available. At the same time, the system may indicate the time when the fitness mode is again available.

In another embodiment, the fitness mode is not disabled during high-traffic times. Instead, the route planning computer 40 takes into account the elevator installation's traffic situation and generates at least one route proposal that serves both the user's trip inquiry and the current high-traffic situation. In view of the trip inquiry, the route planning computer 40 checks if an already planned elevator trip can be used to transport the user 8. For example, if the user's destination floor is floor 7, and an elevator car 34 is already scheduled to go to floor 8, the route planning computer 40 can suggest a route which would include taking take the elevator car 34 going to floor 8, and then taking the stairs back down to floor 7. Similarly, if the user wants to go out for lunch, the route planning computer 40 checks if an elevator car 34 is already scheduled to travel downwards. If this is the case, the route planning computer 40 suggests a route that includes a trip with that elevator car 34. In these examples, the fitness mode is maintained, but the trip-inquiry triggered individual scheduling of elevator trips is restricted during times of high traffic.

As to the preferences of the user 8, for example, the software application on the mobile electronic device 10, or the software program of the route planning computer 40 may allow the user 8 to set certain preferences via a user interface of the mobile electronic device 10 or the floor terminals 12. The user 8 may, for example, specify that the route proposal may or may not include stairs, or how many flights of steps are permitted as a maximum when calculating a route proposal.

In certain embodiments, the mobile device's software application can direct the user 8 via a building map, displayed on the display of the mobile device, along the selected route proposal. In combination with an indoor positioning system, which may be based on the above described beacons 4, the mobile electronic device 10 serves in such an embodiment as a navigation system.

The building 2 may further have visual and/or acoustic indicators distributed throughout the building 2 to provide guidance; they may be provided at elevator landings, doors, and stairwells 6. Such indicators are in one embodiment coupled to the route planning computer 40 that activates the indicators. The route planning computer 40 may identify those indicators that are positioned along the selected route proposal and may activate them sequentially based on the estimated walking time to each one of these indicators. If the indicators include lamps, e.g., lamps with LEDs, the route planning computer 40 may assign a certain color to the selected route proposal, and control the LED lamps to emit light of the assigned color. The user 8 can then follow these lamps along the selected route proposal.

In another embodiment, the indicators may be based on Bluetooth technology, wherein each indicator transmits its identification code. In that embodiment, the mobile electronic device 10 stores the identification codes of all indicators located along the selected route proposal. As the user 8 walks along the selected route proposal and approaches an indicator, the mobile electronic device 10 determines this indicator's identification code and transmits an activation signal to that indicator. In response to the activation signal, the indicator may activate a display, a lamp, or a speaker to assist the user's orientation along the selected route proposal. In one embodiment, the beacons 4 shown in FIG. 1 may serve as such Bluetooth based indicators. One example of a beacon 4 suitable for bidirectional communication with their mobile electronic device 10 is an Enterprise Beacon available from Onyx Beacon Ltd., Romania. Such a beacon has a buzzer to generate an audible acoustic signal, and a sticky side to position the beacon at a desired location.

In accordance with the provisions of the patent statutes, the present invention has been described in what is considered to represent its preferred embodiment. However, it should be noted that the invention can be practiced otherwise than as specifically illustrated and described without departing from its spirit or scope.

The invention claimed is:

1. A method of controlling a system having an elevator controller of an elevator installation in a building, a storage device storing building plan data of the building, and a route planning computer, the method comprising the steps of:

receiving by the route planning computer a trip inquiry from a user at a current location within the building, the trip inquiry including a desired destination and a desired activity parameter, wherein the desired activity parameter is a health/fitness goal expressed as a number by the user when setting up the trip inquiry the trip inquiry further including a request for route options with a particular identification of a desired number of steps for each route option;

reading by the route planning computer building plan data from the storage device, the building plan data including building access doors, hallways, stairs, designated areas, and elevator landings;

determining by the route planning computer the current location of the user within the building;

calculating by the route planning computer at least two route options based on the current location of the user, the building plan data, the desired destination and the desired activity parameter;

communicating by the route planning computer the at least two route options to the user, wherein for each route option an estimated number of steps is communicated;

upon receipt of a confirmation indicative of the user selecting one of the route options, transmitting by the route planning computer a control signal identifying a boarding floor and a destination floor to the elevator controller as determined from the selected route option; and controlling by the elevator controller the elevator installation according to the control signal.

2. The method according to claim 1 wherein the activity parameter includes a desired number of steps to be taken by the user.

3. The method according to claim 1 including conveying the at least two route options to the user using a user interface of a user input device.

4. The method according to claim 3 wherein conveying the at least two route options to the user includes activating the user interface to display the at least two route options as text and/or at least one symbol, or to announce the at least two route options as an audio message.

5. The method according to claim 1 wherein the determining the current location of the user includes using an indoor positioning system, or identifying a location of a floor terminal involved in communicating the trip inquiry to the route planning computer, wherein the location of the floor terminal is documented in the building plan data.

6. The method according to claim 1 including disabling the route planning computer during times of high traffic in the elevator installation.

7. The method according to claim 1 wherein calculating the at least two route options is further based on a traffic situation of the elevator installation, wherein individual scheduling of elevator trips is restricted during times of high traffic in the elevator installation.

8. The method according to claim 1 wherein the controlling the elevator installation includes providing immediate elevator service to a boarding floor, or scheduling elevator service to the boarding floor for a later time taking into account a walking time of the user to the boarding floor.

9. A system comprising:

an elevator controller for controlling an elevator car to transport a user from one floor to another floor in a building, wherein the user carries a mobile electronic device for setting up a user-specific trip inquiry including a desired destination within the building and a desired user activity parameter, wherein the desired user activity parameter is a health/fitness goal expressed as a number by the user when setting up the user-specific trip inquiry the trip inquiry further including a request for route options with a particular identification of a desired number of steps for each route option;

a storage device storing building plan data of the building, the building plan data including locations of building access doors, hallways, stairs, designated areas, and elevator landings; and a route planning computer coupled to the elevator controller and to the storage device, the route planning computer, upon receipt of the user-specific trip inquiry, determining at least two route options based on the building plan data, the desired user activity parameter, and the desired destination, and the route planning computer communicating the at least two route options to the user for the user to confirm selection of one of the route options, wherein for each route option an estimated number of steps is communicated, wherein upon receipt of a confirmation indicative of the user selecting one of the route options, the route planning computer transmits a control signal identifying a boarding floor and a destination floor to the elevator controller as determined from the selected route option, and wherein the elevator controller controls the elevator car according to the control signal.

10. The system according to claim 9 including a floor terminal on each floor of the building at a predetermined location, the predetermined locations being documented in the building plan data, wherein each of the floor terminals is coupled via a network to the elevator controller.

11. The system according to claim 10 wherein each of the floor terminals includes a user interface allowing the user to submit the user-specific trip inquiry, to receive the at least two route options, and to confirm the at least two route options.

12. The system according to claim 9 including indicators distributed throughout the building to provide guidance to the user, wherein each of the indicators is adapted to be activated to emit light or sound.

13. The system according to claim 9 including an indoor positioning system based on Bluetooth beacons.

14. The system according to claim 9 wherein the activity parameter includes a desired number of steps to be taken by the user.

15. A method of controlling a system having an elevator controller of an elevator installation in a building, a storage device storing building plan data of the building, and a route planning computer, the method comprising the steps of:

receiving by the route planning computer a trip inquiry from a user at a current location within the building, the trip inquiry including a desired destination and a desired activity parameter, wherein the desired activity parameter is a health/fitness goal expressed as a number by the user when setting up the trip inquiry, the desired activity parameter indicating at least one of a desired number of steps on a way to the desired destination and a walking time to the desired destination, the trip inquiry further including a request for route options with a particular identification of a desired number of steps for each route option;

reading by the route planning computer building plan data from the storage device, the building plan data including locations of building access doors, hallways, stairs, designated areas, and elevator landings;

determining by the route planning computer the current location of the user within the building;

calculating by the route planning computer at least two route options based on the trip inquiry, the current location of the user, the building plan data, the desired destination and the desired activity parameter expressed as the desired number of steps;

communicating by the route planning computer the at least two route options to the user, wherein for each route option an estimated number of steps is communicated;

upon receipt of a confirmation indicative of the user selecting one of the route options, transmitting by the route planning computer a control signal identifying a boarding floor and a destination floor to the elevator controller as determined from the selected route option, wherein the destination floor is not the desired destination; and controlling by the elevator controller the elevator installation according to the control signal.

16. The method according to claim 15 wherein the desired destination is a specific location in the building including a building entrance or a specific room.

\* \* \* \* \*